US00PP22932P2

(12) United States Plant Patent
Dümmen

(10) Patent No.: US PP22,932 P2
(45) Date of Patent: Aug. 7, 2012

(54) ***PETUNIA* PLANT NAMED 'DUESWEGRICE'**

(50) Latin Name: *Petunia×hybrida*
Varietal Denomination: Dueswegrice

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 22 days.

(21) Appl. No.: 12/930,268

(22) Filed: Dec. 31, 2010

(51) Int. Cl.
*A01H 5/00* (2006.01)

(52) U.S. Cl. ..... Plt./356.18

(58) Field of Classification Search ..... Plt./356.18
See application file for complete search history.

*Primary Examiner* — Susan McCormick Ewoldt
(74) *Attorney, Agent, or Firm* — C. A. Whealy

(57) ABSTRACT

A new and distinct cultivar of *Petunia* plant named 'Dueswegrice', characterized by its mounding and outwardly spreading to trailing plant habit; freely branching habit; early and freely flowering habit; large purple-colored flowers with dark violet-colored venation; and good garden performance.

1 Drawing Sheet

Botanical designation: *Petunia×hybrida.*
Cultivar denomination: 'DUESWEGRICE'.

BACKGROUND OF THE INVENTION

The present invention relates to a new and distinct cultivar of *Petunia* plant, botanically known as *Petunia×hybrida* and hereinafter referred to by the name 'Dueswegrice'.

The new *Petunia* plant is a product of a planned breeding program conducted by the Inventor in Rheinberg, Germany. The objective of the breeding program is to create new trailing *Petunia* plants with numerous unique and attractive flowers.

The new *Petunia* plant originated from a cross-pollination made by the Inventor in July, 2008 in Rheinberg, Germany of a proprietary selection of *Petunia×hybrida* identified as code number T07-5643-12, not patented, as the female, or seed, parent with a proprietary selection of *Petunia×hybrida* identified as code number T05-3223-002, not patented, as the male, or pollen, parent. The new *Petunia* plant was discovered and selected by the Inventor as a single flowering plant within the progeny of the stated cross-pollination in a controlled greenhouse environment in Rheinberg, Germany in May, 2010.

Asexual reproduction of the new *Petunia* plant by terminal cuttings in a controlled greenhouse environment in Rheinberg, Germany since May, 2010 has shown that the unique features of this new *Petunia* plant are stable and reproduced true to type in successive generations.

SUMMARY OF THE INVENTION

Plants of the new *Petunia* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Dueswegrice'. These characteristics in combination distinguish 'Dueswegrice' as a new and distinct *Petunia* plant:

1. Mounding and outwardly spreading to trailing plant habit.

2. Freely branching habit.
3. Early and freely flowering habit.
4. Large purple-colored flowers with dark violet-colored venation.
5. Good garden performance.

Plants of the new *Petunia* can be compared to plants of the female parent selection. Plants of the new *Petunia* differ primarily from plants of the female parent selection in flower color as plants of the female parent selection have pink-colored flower venation. In addition, plants of the new *Petunia* are more vigorous than plants of the female parent selection.

Plants of the new *Petunia* can be compared to plants of the male parent selection. Plants of the new *Petunia* differ primarily from plants of the male parent selection in flower color as plants of the male parent selection have lighter violet-colored flower venation.

Plants of the new *Petunia* can be compared to plants of the *Petunia×hybrida* 'Sanguna Plum Vein', not patented. In side-by-side comparisons conducted in Rheinberg, Germany, plants of the new *Petunia* differed primarily from plants of 'Sanguna Plum Vein' in the following characteristics:

1. Plants of the new *Petunia* were more compact than plants of 'Sanguna Plum Vein'.
2. Plants of the new *Petunia* had smaller flowers than plants of 'Sanguna Plum Vein'.
3. Plants of the new *Petunia* had shorter peduncles than plants of 'Sanguna Plum Vein'.

BRIEF DESCRIPTION OF THE PHOTOGRAPH

The accompanying colored photograph illustrates the overall appearance of the new *Petunia* plant showing the colors as true as it is reasonably possible to obtain in colored reproductions of this type. Colors in the photograph may differ slightly from the color values cited in the detailed botanical description which accurately describe the colors of the new *Petunia* plant.

The photograph comprises a side perspective view of typical flowers, flower buds and leaves of 'Dueswegrice'.

DETAILED BOTANICAL DESCRIPTION

The aforementioned photograph and following observations, measurements and values describe plants grown during the summer in 10.5-cm containers in a glass-covered greenhouse in Rheinberg, Germany and under commercial production practices. During the production of the plants, day and night temperatures averaged 18° C. and light levels averaged 4,500 lux. Plants were pinched one time three weeks after planting and were 16 weeks old when the photograph and description were taken. In the following description, color references are made to The Royal Horticultural Society Colour Chart, 1995 Edition, except where general terms of ordinary dictionary significance are used.

Botanical classification: *Petunia×hybrida* 'Dueswegrice'.

Parentage:

*Female, or seed, parent*.—Proprietary selection of *Petunia×hybrida* identified as code number T07-5643-12, not patented.

*Male, or pollen, parent*.—Proprietary selection of *Petunia×hybrida* identified as code number T05-3223-002, not patented.

Propagation:

*Type*.—By terminal cuttings.

*Time to initiate roots, summer*.—About five days at temperatures of 20° C.

*Time to initiate roots, winter*.—About seven days at temperatures of 20° C.

*Time to produce a rooted young plant, summer*.—About three weeks at temperatures of 20° C.

*Time to produce a rooted young plant, winter*.—About four weeks at temperatures of 20° C.

*Root description*.—Fine, fibrous; white in color.

*Rooting habit*.—Freely branching; dense.

Plant description:

*Plant and growth habit*.—Mounding and outwardly spreading to trailing plant habit; freely branching habit with about eight to ten lateral branches developing after pinching; moderately vigorous growth habit.

*Plant height*.—About 10 cm.

*Plant diameter*.—About 12 cm.

Lateral branch description:

*Length*.—About 9 cm.

*Diameter*.—About 9 mm.

*Internode length*.—About 1.4 cm.

*Strength*.—Moderately strong.

*Aspect*.—Initially upright to outwardly spreading.

*Texture*.—Pubescent.

*Color*.—Close to 144A to 144B.

Foliage description:

*Arrangement*.—Before flowering, alternate, simple; after flowering, opposite, simple.

*Length*.—About 3.9 cm.

*Width*.—About 2.2 cm.

*Shape*.—Spatulate.

*Apex*.—Obtuse.

*Base*.—Attenuate.

*Margin*.—Entire.

*Texture, upper and lower surfaces*.—Pubescent; leathery.

*Venation pattern*.—Pinnate; arcuate.

*Color*.—Developing leaves, upper surface: Close to 137B. Developing leaves, lower surface: Close to 137C. Fully expanded leaves, upper surface: Close to 137A; venation, close to 144B. Fully expanded leaves, lower surface: Close to 137C; venation, close to 144B.

*Petioles*.—Length: About 1.1 cm. Diameter: About 4.4 mm. Texture, upper and lower surfaces: Pubescent. Color, upper surface: Close to 144A. Color, lower surface: Close to 144B.

Flower description:

*Flower arrangement and habit*.—Large salverform flowers; single flowers arising from leaf axils; freely flowering habit with usually about 25 to 30 open flowers and flower buds per plant; flowers face mostly upright to outwardly.

*Fragrance*.—None detected.

*Natural flowering season*.—Plants flower continuously during the spring and summer in Germany; early flowering habit, plants typically beginning flowering about nine weeks after planting.

*Flower longevity*.—Individual flowers last about five to six days on the plant; flowers persistent.

*Flower diameter*.—About 6.4 cm.

*Flower length (height)*.—About 3 cm.

*Flower throat diameter*.—About 9 mm.

*Flower tube length*.—About 2.3 cm.

*Flower tube diameter*.—About 3 mm.

*Flower bud*.—Shape: Ovoid. Length: About 3.8 cm. Diameter: About 8.75 mm. Color: Close to 78A.

*Corolla*.—Arrangement: Five petals fused at the base and opening into a flared trumpet. Petal lobe length (from throat): About 2.7 cm. Petal lobe width: About 3.1 cm. Petal shape: Roughly spatulate. Petal apex: Rounded. Petal margin: Entire. Petal texture, upper and lower surfaces: Rippled, glabrous. Throat texture: Rippled, glabrous. Tube texture: Rippled, pubescent. Color: Petal lobe, when opening, upper surface: Close to 77A. Petal lobe, when opening, lower surface: Close to 77B. Petal lobe, fully opened, upper surface: Close to 77A to 77B; venation, close to 83A; color becoming closer to 81A with development. Petal lobe, fully opened, lower surface: Close to 77B; venation, close to 83B. Flower throat: Close to 79A; venation, close to 83A. Flower tube: Close to 79B; venation, close to 83A.

*Calyx*.—Arrangement: Five sepals fused at the base forming a star-shaped calyx. Sepal length: About 2.1 cm. Sepal width: About 2.75 mm. Sepal shape: Oblong. Sepal apex: Rounded. Sepal margin: Entire. Sepal texture, upper and lower surfaces: Smooth. Color, immature and mature, upper surface: Close to 137C. Color, immature and mature, lower surface: Close to 137D.

*Peduncles*.—Length: About 2.8 cm. Diameter: About 1.5 mm. Strength: Moderately strong. Texture: Smooth. Color: Close to 144B.

*Reproductive organs*.—Stamens: Quantity: Five per flower. Filament length: About 1.2 cm. Filament color: Close to 155A. Anther shape: Ovate. Anther length: About 1.5 mm. Anther color: Close to 189D. Pollen amount: Abundant. Pollen color: Close to 115A. Pistils: Quantity: One per flower. Pistil length: About 2.4 cm. Style length: About 1.9 cm. Style color: Close to 144B. Stigma shape: Rounded. Stigma color: Close to 144A. Ovary color: Close to 144B. Seed/fruit: Seed and fruit development have not been observed on plants of the new *Petunia*.

Garden performance: Plants of the new *Petunia* have been observed to have good garden performance and tolerate wind, rain and temperatures ranging from about 5° C. to about 40° C.

Pathogen/pest resistance: Plants of the new *Petunia* have not been observed to be resistant to pathogens and pests common to *Petunia.*

It is claimed:

1. A new and distinct *Petunia* plant named 'Dueswegrice' as illustrated and described.

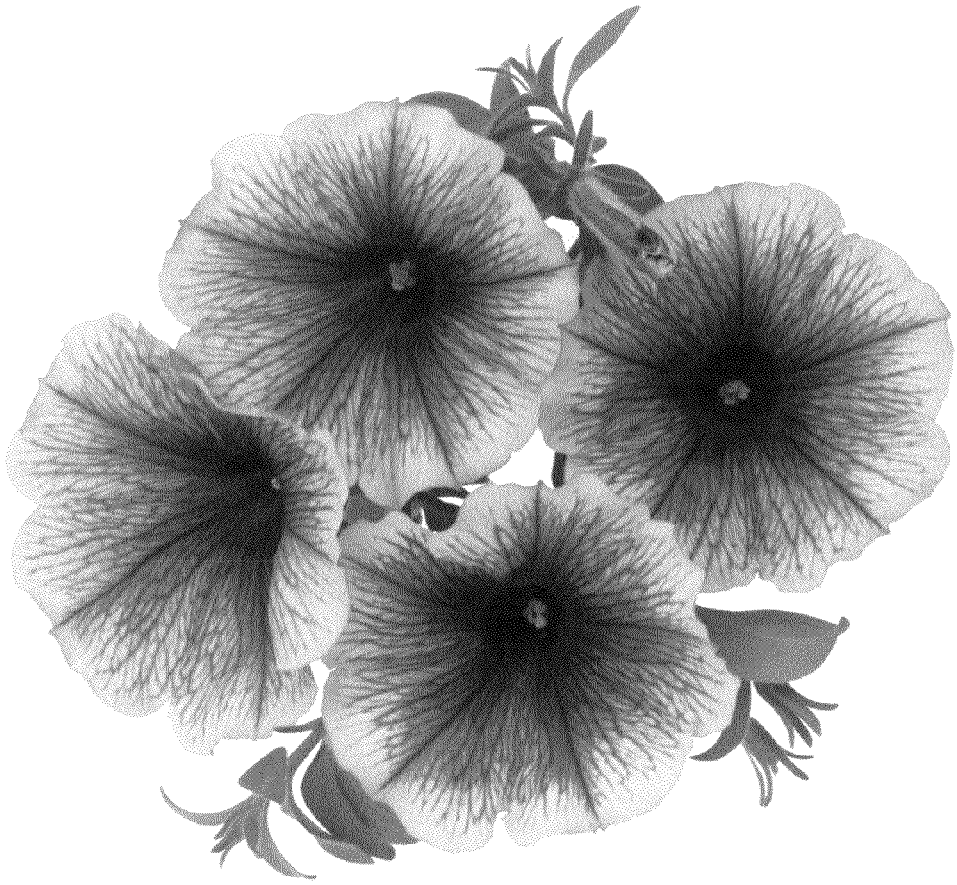

* * * * *